US008007778B2

(12) United States Patent
Dillmann et al.

(10) Patent No.: US 8,007,778 B2
(45) Date of Patent: Aug. 30, 2011

(54) USE OF CALCIUM BINDING PROTEINS TO IMPROVE CARDIAC CONTRACTILE FUNCTION

(75) Inventors: Wolfgang H. Dillmann, Solana Beach, CA (US); Jorge Suarez, San Diego, CA (US); Darrell Belke, San Diego, CA (US); Bernd Gloss, Chapel Hill, NC (US)

(73) Assignee: The Regents of the University of California, Oakland, CA (US)

( * ) Notice: Subject to any disclaimer, the term of this patent is extended or adjusted under 35 U.S.C. 154(b) by 1064 days.

(21) Appl. No.: 10/562,524

(22) PCT Filed: Jun. 28, 2004

(86) PCT No.: PCT/US2004/022718
§ 371 (c)(1),
(2), (4) Date: Sep. 13, 2006

(87) PCT Pub. No.: WO2005/003323
PCT Pub. Date: Jan. 13, 2005

(65) Prior Publication Data
US 2007/0041942 A1    Feb. 22, 2007

Related U.S. Application Data

(60) Provisional application No. 60/484,509, filed on Jul. 1, 2003.

(51) Int. Cl.
*A61K 48/00*    (2006.01)
*C12Q 1/68*    (2006.01)

(52) U.S. Cl. .......... 424/93.1; 514/44 R; 435/6
(58) Field of Classification Search .............. None
See application file for complete search history.

(56) References Cited

U.S. PATENT DOCUMENTS
6,335,011 B1 *    1/2002    Podsakoff et al. ........... 424/93.2

OTHER PUBLICATIONS

Kizana et al. Heart, Lung and Circulation 2007;16:180-184.*
Seidler et al. Circ Res. 2003;93:132-139.*
Fisher et al., "Overexpression of Sorcin in the Murine Heart Modulates Cardiac Performance, Circulation", Oct. 2000, vol. 102, No. 18, p. 296, 1448.
Suarez et al., "In vivo Adenoviral Gene Transfer of Sorcin Increases Cardiac Contractility Circulation", Nov. 2002, vol. 106, No. 19, Supp. p. 29, 144.
Suarez et al., "In vivo adenoviral transfer of sorcin reverses cardiac contractile abnormalities of diabetic cardiomyopathy", Am. J. Physiol. Heart Circ. Physiol., Jan. 2004; 286(1):H68-75, Epub. Sep. 4, 2003.

* cited by examiner

*Primary Examiner* — Doug Schultz
(74) *Attorney, Agent, or Firm* — DLA Piper US (LLP)

(57) ABSTRACT

Methods useful in the regulation of myocardial contraction are disclosed. The methods are useful in the regulation of heart function. The invention reveals that sorcin overexpression enhances cardiac contractile performance and establishes the concept of sorcin as a regulator of myocardial contractility. The invention also provides screening assays that allow for the identification of agents that modulate sorcin expression. Such agents are useful, for example, for diagnosing cardiac contractile function associated disorders in subjects, and treating the subjects with the agents identified as being able to modulate sorcin expression.

10 Claims, 3 Drawing Sheets

USE OF CALCIUM BINDING PROTEINS TO IMPROVE CARDIAC CONTRACTILE FUNCTION

CROSS REFERENCE TO RELATED APPLICATIONS

This application is a 35 USC §371 National Stage application of PCT Application No. PCT/US2004/022718 filed Jun. 28, 2004; which claims the benefit under 35 USC §119(e) to U.S. Application Ser. No. 60/484,509 filed Jul. 1, 2003, now abandoned. The disclosure of the prior application is considered part of and is incorporated by reference in the disclosure of this application.

GRANT INFORMATION

This invention was made with government support under Grant Nos. HL52946 and HL66917 awarded by the National Institutes of Health. The government has certain rights in the invention.

FIELD OF THE INVENTION

The invention relates generally to regulation of myocardial contraction and, more specifically, to improvement of cardiac contraction via administration of the Calcium binding EF hand protein, sorcin.

BACKGROUND INFORMATION

Congestive heart failure is an important medical problem resulting in significant morbidity and mortality. Heart failure occurs at an increased incidence in patients with diabetes mellitus. In addition to an increased propensity for coronary vascular disease, resulting in an ischemic heart disease, a diabetic cardiomyopathy occurs in combination with or independent of coronary vascular disease. In the diabetic heart, abnormal $Ca^{2+}$ handling during the contractile cycle results in a decreased upstroke phase of the $Ca^{2+}$ transient due to diminished release of $Ca^{2+}$ from the sarcoplasmic reticulum (SR) by the ryanodine receptor (RyR2) (22). In addition, the diastolic decline of the $Ca^{2+}$ transient is diminished due to a reduced activity of the SERCA2a pump (4). Recently developed approaches are aimed at improving the abnormal $Ca^{2+}$ flux of the heart using viral vector based delivery of proteins to cardiac myocytes, resulting in normalization of the $Ca^{2+}$ transient and improved contractile function. The identification of novel calcium modulating proteins suitable for viral vector based delivery is therefore of interest to gain additional insight into the components governing calcium homeostasis in the cardiac myocyte and to potentially provide novel strategies for therapeutic intervention to achieve improved contractile function.

One such calcium modulating protein is sorcin, a 21.6 kDa $Ca^{2+}$ binding protein which is a member of the penta EF-hand family (11). Sorcin)was initially identified in multidrug-resistance cells, where it is overexpressed due to a shared locus encompassing both the multidrug-resistance P-glycoprotein (mdr1) and the sorcin gene (12). Sorcin is expressed in a wide variety of mammalian tissues, including heart and skeletal muscle (13). However, the function of sorcin remains speculative both related to multidrug resistance and to other functions, derived from its effects in excitable cells like neurons (6) and skeletal muscle (14). Sorcin has a wide tissue distribution and highly conserved amino acid sequence among species suggesting that its biological role transcends its potential involvement in multidrug resistance.

Sorcin translocates from the cytosol to membranes upon binding of calcium. Translocation takes place at micromolar calcium concentrations, and it is reversed when the cation concentration is lowered by addition of EGTA (15, 27). Translocation from the cytosol to membranes allows sorcin to interact with specific target proteins. In cardiac cells, sorcin localizes to junctions between the transverse tubule system and junctional sarcoplasmic reticulum and antisera against either sorcin or the cardiac RyA2 precipitate both proteins (13). Furthermore, sorcin decreases the open probability of single RyR2 reconstituted in lipid bilayers (9). Therefore, sorcin may play a role in modulating intracellular $Ca^{2+}$ levels in the heart (25). More recently, an association of sorcin with the pore-forming subunit of voltage-dependent L-type $Ca^{2+}$ channels was found (14), however, the functional implication of this association is unknown.

SUMMARY OF THE INVENTION

The present invention relates to regulation of cardiac contractile function. The present invention is based on the discovery that administration or overexpression of the protein sorcin enhances cardiac contractile function. Accordingly, the present invention relates to methods of increasing cardiac contractile function by stimulating sorcin expression or overexpression. The invention further provides methods to identify agents that can modulate sorcin expression, including high throughput screening methods, and provides a means to identify agents that are useful for treating patients having cardiac contractile function associated disorders, including agents that are useful for a particular patient, thus allowing for personalized medicine.

Thus, in one embodiment, the invention provides a method of increasing cardiac contractile function in a subject by altering the expression of sorcin in the heart. In one aspect, the alteration of expression is performed by administration of a vector encoding sorcin to the subject, where the sorcin is expressed or overexpressed and increases contractile function. In another aspect, the vector is an adenoviral vector and may be administered directly into the heart of the subject. Although the heart may be normal, the subject may be suffer from diabetes mellitus. In another aspect, the heart has decreased contractile function.

In another embodiment, the invention provides a method of altering sorcin expression by administering an agent that modulates sorcin expression. In one aspect, the agent stimulates socin overexpression. In another aspect, the agent is administered in a pharmaceutically acceptable carrier.

In another embodiment, the invention provides a method of treating or preventing heart failure, by administering an adenoviral vector encoding sorcin to a subject. The vector encoding sorcin may be administered directly into the heart of the subject, and cause overexpression of sorcin.

In another embodiment, the invention provides a method of identifying an agent that modulates sorcin expression. A sample comprising sorcin is brought into contact with a test agent under conditions sufficient for sorcin expression. Any detected change in sorcin expression in the presence of the test agent as compared to the sorcin expression in the absence of the test agent identifies the test agent as an agent that modulates sorcin expression. In one aspect, the sample is a cell sample that may be obtained from a subject. In another aspect, the sample is a cell free sample. In another aspect, the agent stimulates sorcin overexpression. In another aspect, an agent so identified is used for treating or preventing heart failure in a subject.

In another embodiment, the invention provides a method of identifying an agent that modulates cardiac contractile function by administering the agent to a heart and measuring the maximum speed of contraction and the maximum speed of relaxation, where an increase in maximum speed is indicative of an agent that modulates cardiac contractile function. In another aspect, an agent so identified is used for treating or preventing heart failure in a subject.

In another embodiment, the invention provides a method of diagnosing a cardiac contractile function associated disorder in a subject by comparing the sorcin expression in a test sample from the subject with the sorcin expression in a corresponding normal sample, where a difference in sorcin expression in the test sample as compared to the sorcin expression in the normal sample is diagnostic of a cardiac contractile function associated disorder in the subject. Accordingly, the invention further provides a method for monitoring a therapeutic regimen for treating a subject having heart failure by determining a change in sorcin expression during therapy.

DETAILED DESCRIPTION OF THE INVENTION

Figure 1:
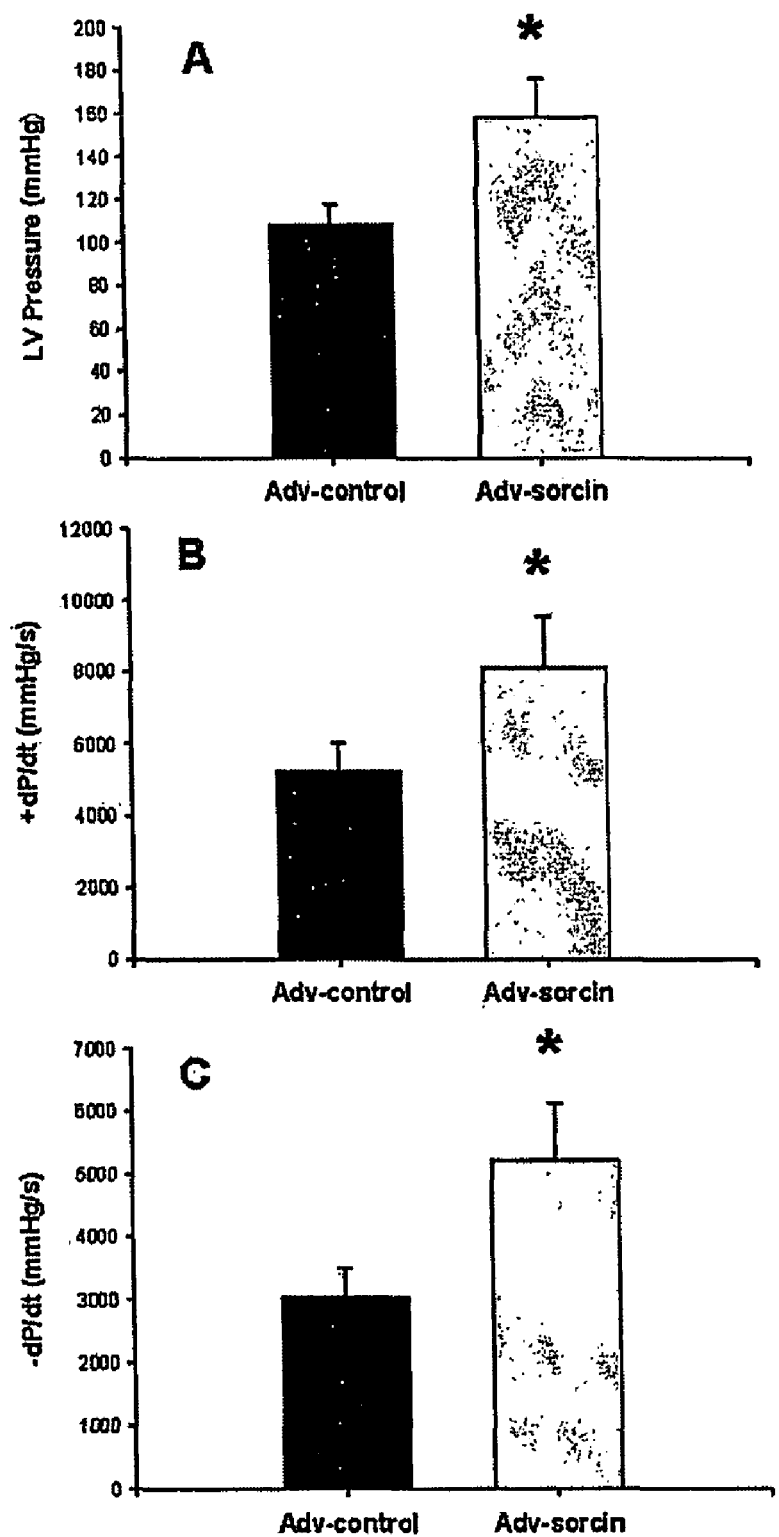
FIG. 1 illustrates the influence of sorcin overexpression on myocardial contractility determined in isolated perfused hearts. Cardiac performance was evaluated after 5 days of injection of Adv-control or Adv-sorcin: a) peak systolic pressure; b) inotropic effect of sorcin; and c) lusitropic effect. Values correspond to the mean±SE of 5 mice in each group.

In the present invention it was discovered that sorcin participates in regulating calcium homeostasis in the cardiac cell and that alterations in the expression of sorcin contribute to impaired sarcoplasmic $Ca^{2+}$ handling in pathological states of the myocardium and therefore contribute to contractile function. Based on this discovery, the invention provides a method of increasing cardiac contractile function in a subject; a method of treating or preventing heart failure; and a method of identifying an agent that modulates cardiac contractile function. In one aspect, the methods of the invention are useful in subjects with diabetes mellitus.

The present invention is not limited to the particular methodology, protocols, cell lines, vectors, reagents, etc., described herein, as these may vary. It is also to be understood that the terminology used herein is used for the purpose of describing particular embodiments only, and is not intended to limit the scope of the present invention. As used herein and in the appended claims, the singular forms "a," "an," and "the" include plural reference unless the context clearly dictates otherwise. Thus, for example, a reference to "an antibody" is a reference to one or more antibodies and equivalents thereof (e.g., antigen binding antibody fragments) known to those skilled in the art, and so forth.

In exemplary methods of the present invention, as set forth in the attached Exhibit A, sorcin-encoding nucleic acid was overexpressed in the heart of either normal or diabetic mice and in adult rat cardiomyocytes using an adenoviral gene transfer approach. Sorcin overexpression was associated with an increase in cardiac contractility of the normal heart and dramatically rescued the abnormal contractile function of the diabetic heart. These effects could be attributed to an improvement of the calcium transients found in the cardiomyocyte after sorcin overexpression. Viral vector mediated delivery of sorcin to cardiac myocytes is beneficial resulting in improved contractile function in diabetic cardiomyopathy. As such, sorcin administration is useful in methods of increasing cardiac contractile function and treating or preventing heart failure in subjects. In particular, administration of sorcin is particularly useful in the treatment of failing hearts in subjects with diabetes.

As used herein, the term "disorder" or "disease" refers to any condition resulting in decreased cardiac contractile function. The term "cardiac contractile function associated disease" or "cardiac contractile function associated disorder" is used herein to refer specifically to a condition in which cardiac contractile function is decreased below the level of cardiac contractile function in a corresponding normal heart cell due to depressed levels of sorcin. Cardiac contractile function associated disorders include, but are not limited to, cardiomyopathy, cardiovascular disorders, sleep disorders, obesity, excessive scarring resulting from acute or repetitive traumas, including surgery or radiation therapy, fibrosis of organs including scleroderma, keloids, and hypertrophic scarring. Abnormal levels of sorcin can be associated with general tissue scarring, tumor-like growths in the skin, and sustained scarring of blood vessels, leading to impaired blood-carrying ability, hypertension, hypertrophy, etc.

As used herein, the term "contractile function" refers to the ability of the heart to contract, by which the muscle increases in tension. The normal contractile function of the heart involves a regular contraction and release pattern.

It is well established that the increase in cytosolic $Ca^{2+}$ during systole occurs by release of $Ca^{2+}$ from the sarcoplasmic reticulum through a specialized release channel, the ryanodine receptor, via the process of $Ca^{2+}$-induced $Ca^{2+}$ release (CICR) (3). The entry of a small amount of ("trigger") $Ca^{2+}$ through the sarcolemmal L-type $Ca^{2+}$ current ($I_{Ca}$) produces a localized increase of $[Ca^{2+}]_i$ in the small space between the surface and SR membranes. This increases the open probability of the RyR2, resulting in the efflux of $Ca^{2+}$ from the SR into the cytoplasm. Amplification of $I_{Ca}$ by CICR elevates myoplasmic $Ca^{2+}$ concentrations to initiate muscle contraction. Relaxation is initiated by a lowering of $[Ca^{2+}]_i$ produced either by pumping back $Ca^{2+}$ into the SR by the SR $Ca^{2+}$-ATPase or out or the cell, largely by the sarcolemmal $Na^+$—$Ca^{2+}$ exchange.

In many types of heart failure cardiac myocyte calcium handling is abnormal due to downregulation of key calcium-handling proteins like the $Ca^{2+}$ ATPase of the sarcoplasmic reticulum (SERCA2a) and ryanodine receptor (RyR2). The alteration in SERCA2a and RyR2 expression results in altered cytosolic calcium transients leading to abnormal contraction. An interruption of the heart's ability to release $Ca^{2+}$ from the SR during systole results in decreased contractile function, which is associated with congestive heart failure. Present treatment options for congestive heart failure range from dietary restrictions to cardiac transplantation. The present invention provides an alternate treatment. Accordingly, a method of treating or preventing heart failure by administration of an adenoviral vector encoding sorcin to a subject to alter contractile function in the subject is provided.

As used herein, the term "vector" refers to a nucleic acid molecule into which another nucleic acid fragment can be integrated without loss of the vector's ability to self-replicate. Vectors may originate from a virus, a plasmid of the cell of a higher organism. Vectors are utilized to introduce foreign DNA into a host cell, wherein the vector is replicated.

A polynucleotide agent can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes a peptide, for expressing the encoded peptide in a particular cell. An expression vector can contain the expression elements necessary to achieve, for example, sustained transcription of the encoding polynucleotide, or the regulatory elements can be operatively linked to the polynucleotide prior to its being cloned into the vector.

As used herein, "polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- an double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

As used herein, "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626-646 and Rattan et al., "Protein Synthesis: Posttranslational Modifications and Aging", Ann NY Acad Sci (1992) 663:48-62.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzymol., Vol. 185, Goeddel, ed. (Academic Press, Inc., 1990); Jolly, Canc. Gene Ther. 1:51-64, 1994; Flotte, J. Bioenerg. Biomemb. 25:37-42, 1993; Kirshenbaum et al., J. Clin. Invest. 92:381-387, 1993; each of which is incorporated herein by reference).

A polynucleotide useful in a method of the invention also can be operatively linked to tissue specific regulatory element, for example, a neuron specific regulatory element, such that expression of an encoded peptide agent is restricted to neurons in an individual, or to neurons in a mixed population of cells in culture, for example, an organ culture. For example, neuronal promoters such as the myelin basic protein promoter and other neuronal-specific promoters known to those of skill in the art may be used for neuronal cells. Muscle-regulatory elements including, for example, the muscle creatine kinase promoter (Sternberg et al., *Mol. Cell. Biol.* 8:2896-2909, 1988, which is incorporated herein by reference) and the myosin light chain enhancer/promoter (Donoghue et al., *Proc. Natl. Acad. Sci., USA* 88:5847-5851, 1991, which is incorporated herein by reference) are well known in the art. A variety of other promoters have been identified which are suitable for up regulating expression in cardiac tissue. Included, for example, are the cardiac I-myosin heavy chain (AMHC) promoter and the cardiac I-actin promoter. Other examples of tissue-specific regulatory elements include, tissue-specific promoters, pancreatic (insulin or elastase), and actin promoter in smooth muscle cells.

Viral expression vectors can be particularly useful for introducing a polynucleotide useful in a method of the invention into a cell, particularly a cell in a subject. Viral vectors provide the advantage that they can infect host cells with relatively high efficiency and can infect specific cell types. For example, a polynucleotide encoding a sorcin protein or functional peptide portion thereof can be cloned into a baculovirus vector, which then can be used to infect an insect host cell, thereby providing a means to produce large amounts of the encoded protein or peptide portion. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpes virus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242, 1997; Wilson, *New Engl. J. Med.* 334:1185-1187 (1996), each of which is incorporated herein by reference). In one aspect of the invention, an adenovirus vector is utilized. Adenoviruses are double-stranded DNA viruses, where both strands of DNA encode genes. The genome encodes about thirty proteins. In another aspect of the invention, an adeno-associated virus vector is utilized.

Preferred viral vectors are derived from adenovirus (Ad) or adeno-associated virus (AAV). The term "adenovirus" refers to over 40 adenoviral subtypes isolated from humans, and as many from other mammals and birds. See, Strauss, "Adenovirus infections in humans," in *The Adenoviruses*, Ginsberg, ed., Plenum Press, New York, N.Y., pp. 451-596 (1984). Recombinant adenovirus vectors, such as those based on the human adenovirus 5 (as described by McGrory W J, et al., Virology 163: 614-617, 1988) are missing essential early genes from the adenovirus genome (usually E1A/E1B), and are therefore unable to replicate unless grown in permissive cell lines that provide the missing gene products in trans. In place of the missing adenovirus genomic sequences, a transgene of interest can be cloned and expressed in tissue/cells infected with the replication-defective adenovirus. Although adenovirus-based gene transfer does not generally result in stable integration of the transgene into the host genome (less than 0.1% adenovirus-mediated transfections result in transgene incorporation into host DNA), adenovirus vectors can be propagated in high titer and transfect non-replicating cells; and, although the transgene is not passed to daughter cells, this is suitable for gene transfer to adult cardiac myocytes, which do not actively divide. Retrovirus vectors provide stable gene transfer, and high titers are now obtainable via retrovirus pseudotyping (Burns, et al., *Proc. Natl. Acad. Sci.* (USA) 90: 8033-8037, 1993), but current retrovirus vectors are generally unable to efficiently transduce nonreplicating cells Additional references describing adenovirus vectors and other viral vectors which could be used in the methods of the present invention include the following: Horwitz, M. S., Adenoviridae and Their Replication, in Fields, B., et al. (eds.) *Virology*, Vol. 2, Raven Press New York, pp. 1679-1721, 1990); Graham, F., et al., pp. 109-128 in *Methods in Molecular Biology*, Vol. 7: Gene Transfer and Expression Protocols, Murray, E. (ed.), Humana Press, Clifton, N.J. (1991); Miller, N., et al., FASEB Journal 9: 190-199, 1995; Schreier, H, *Pharmaceutica Acta Helvetiae* 68: 145-159, 1994; Schneider and French, Circulation 88:1937-1942, 1993; Curiel D. T., et al., *Human Gene Therapy* 3: 147-154, 1992; Graham, F. L., et al., WO 95/00655 (5 Jan. 1995); Falck-Pedersen, E. S., WO 95/16772 (22 Jun. 1995); Denefle, P. et al., WO 95/23867 (8 Sep. 1995); Haddada, H. et al., WO 94/26914 (24 Nov. 1994); Perricaudet, M. et al., WO 95/02697 (26 Jan. 1995); Zhang, W., et al., WO 95/25071 (12 Oct. 1995). A variety of adenovirus plasmids are also available from commercial sources, including, e.g., Microbix Biosystems of Toronto, Ontario (see, e.g., Microbix Product Information Sheet: Plasmids for Adenovirus Vector Construction, 1996).

Additional references describing AAV vectors which could be used in the methods of the present invention include the following: Carter, B., *Handbook of Parvoviruses*, vol. I, pp. 169-228, 1990; Berns, *Virology*, pp. 1743-1764 (Raven Press 1990); Carter, B., *Curr. Opin. Biotechnol.*, 3: 533-539, 1992; Muzyczka, N., *Current Topics in Microbiology and Immunology*, 158: 92-129, 1992; Flotte, T. R., et al., *Am. J. Respir. Cell Mol. Biol.* 7:349-356, 1992; Chatterjee. et al., *Ann. NY Acad. Sci.*, 770: 79-90, 1995; Flotte, T. R., et al., WO 95/13365 (18 May 1995); Trempe, J. P., et al., WO 95/13392 (18 May 1995); Kotin, R., *Human Gene Therapy*, 5: 793-801, 1994; Flotte, T. R., et al., *Gene Therapy* 2:357-362, 1995; Allen, J. M., WO 96/17947 (13 Jun. 1996); and Du et al., *Gene Therapy* 3: 254-261, 1996.

When retroviruses, for example, are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

A polynucleotide, which can be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biolog*. John Wiley and Sons, Baltimore, Md. (1987, and supplements through 1995), each of which is, incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. Other vectors, such as adeno-associated viruses can have greater host cell range and, therefore, can be used to infect various cell types, although viral or non-viral vectors also can be modified with specific receptors or ligands to alter target specificity through receptor mediated events.

A polynucleotide sequence encoding a sorcin protein can be expressed in either prokaryotes or eukaryotes. Hosts can include microbial, yeast, insect and mammalian organisms. Methods of expressing polynucleotides having eukaryotic or viral sequences in prokaryotes are well known in the art, as are biologically functional viral and plasmid DNA vectors capable of expression and replication in a host. Methods for constructing an expression vector containing a polynucleotide of the invention are well known, as are factors to be considered in selecting transcriptional or translational control signals, including, for example, whether the polynucleotide is to be expressed preferentially in a particular cell type or under particular conditions (see, for example, Sambrook et al., supra, 1989).

A variety of host cell/expression vector systems can be utilized to express a sorcin polypeptide coding sequence, including, but not limited to, microorganisms such as bacteria transformed with recombinant bacteriophage DNA, plasmid DNA or cosmid DNA expression vectors; yeast cells transformed with recombinant yeast expression vectors; plant cell systems infected with recombinant virus expression vectors such as a cauliflower mosaic virus or tobacco mosaic virus, or transformed with recombinant plasmid expression vector such as a Ti plasmid; insect cells infected with recombinant virus expression vectors such as a baculovirus; animal cell systems infected with recombinant virus expression vectors such as a retrovirus, adenovirus or vaccinia virus vector; and transformed animal cell systems genetically engineered for stable expression. -Where the expressed sorcin protein is post-translationally modified, for example, by glycosylation, it can be particularly advantageous to select a host cell/expression vector system that can effect the desired modification, for example, a mammalian host cell/expression vector system.

Depending on the host cell/vector system utilized, any of a number of suitable transcription and translation elements, including constitutive and inducible promoters, transcription enhancer elements, transcription terminators, and the like can be used in the expression vector (Bitter et al., *Meth. Enzymol.* 153:516-544, 1987). For example, when cloning in bacterial systems, inducible promoters such as pL of bacteriophage, plac, ptrp, ptac (ptrp-lac hybrid promoter) and the like can be used. When cloning in mammalian cell systems, promoters derived from the genome of mammalian cells, for example, a human or mouse metallothionein promoter, or from mammalian viruses, for example, a retrovirus long terminal repeat, an adenovirus late promoter or a vaccinia virus 7.5K promoter, can be used. Promoters produced by recombinant DNA or synthetic techniques can also be used to provide for transcription of the inserted GDF receptors coding sequence.

In yeast cells, a number of vectors containing constitutive or inducible promoters can be used (see Ausubel et al., supra, 1987, see chapter 13; Grant et al., *Meth. Enzymol.* 153:516-544, 1987; Glover, *DNA Cloning* Vol. II (IRL Press, 1986), see chapter 3; Bitter, *Meth. Enzymol.* 152:673-684, 1987; see, also, *The Molecular Biology of the Yeast Saccharomyces* (Eds., Strathern et al., Cold Spring Harbor Laboratory Press, 1982), Vols. I and II). A constitutive yeast promoter such as ADH or LEU2 or an inducible promoter such as GAL can be used (Rothstein, *DNA Cloning* Vol. II (supra, 1986), chapter 3). Alternatively, vectors can be used which promote integration of foreign DNA sequences into the yeast chromosome.

Eukaryotic systems, particularly mammalian expression systems, allow for proper post-translational modifications of expressed mammalian proteins. Eukaryotic cells which possess the cellular machinery for proper processing of the primary transcript, glycosylation, phosphorylation, and advantageously, plasma membrane insertion of the gene product can be used as host cells for the expression of a sorcin protein, or functional peptide portion thereof.

Mammalian cell systems which utilize recombinant viruses or viral elements to direct expression can be engineered. For example, when using adenovirus expression vectors, the sorcin polypeptide coding sequence can be ligated to an adenovirus transcription/translation control complex, e.g., the late promoter and tripartite leader sequence; Alternatively, the vaccinia virus 7.5K promoter can be used (Mackett et al., *Proc. Natl. Acad. Sci., USA* 79:7415-7419, 1982; Mackett et al., *J. Virol.* 49:857-864, 1984; Panicali et al., *Proc. Natl. Acad. Sci., USA* 79:4927-4931, 1982). Particularly useful are bovine papilloma virus vectors, which can replicate as extrachromosomal elements (Sarver et al., *Mol. Cell. Biol.* 1:486,.1981). Shortly after entry of this DNA into mouse cells, the plasmid replicates to about 100 to 200 copies per cell. Transcription of the inserted cDNA does not require integration of the plasmid into the host cell chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the sorcin protein gene in host cells (Cone and Mulligan, *Proc. Natl. Acad. Sci., USA* 81:6349-6353, 1984). High level expression, can also be achieved using inducible promoters, including, but not limited to, the metallothionein IIA promoter and heat shock promoters.

For long term, high yield production of recombinant proteins, stable expression is preferred. Rather than using expression vectors which contain viral origins of replication, host cells can be transformed with sorcin protein cDNA controlled by appropriate expression control elements such as promoter, enhancer, sequences, transcription terminators, and polyadenylation sites, and a selectable marker. The selectable marker in the recombinant plasmid can confer resistance to the selection, and allows cells to stably integrate the plasmid into their chromosomes and grow to form foci, which, in turn can be cloned and expanded into cell lines. For example, following the introduction of foreign DNA, engineered cells can be allowed to grow for 1 to 2 days in an enriched media, and then are switched to a selective media. A number of selection systems can be used, including, but not limited to, the herpes simplex virus thymidine kinase (Wigler et al., *Cell* 11:223, 1977), hypoxanthine-guanine phosphoribosyltransferase (Szybalska and Szybalski, *Proc. Natl. Acad. Sci., USA* 48:2026, 1982), and adenine phosphoribosyltransferase (Lowy, et al., *Cell* 22:817, 1980) genes can be employed in tk-, hgprt- or aprt-cells respectively. Also antimetabolite resistance can be used as the basis of selection for dhfr, which confers resistance to methotrexate (Wigler, et al., *Proc. Natl. Acad. Sci. USA* 77:3567, 1980; O'Hare et al., *Proc. Natl. Acad. Sci., USA* 78: 1527, 1981); gpt, which confers resistance to mycophenolic acid (Mulligan and Berg, *Proc. Natl. Acad. Sci., USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1984) genes. Additional selectable genes, including trpB, which allows cells to utilize indole in place of tryptophan; hisD, which allows cells to utilize histinol in place of histidine (Hartman and Mulligan, *Proc. Natl. Acad. Sci., USA* 85:8047, 1988); and ODC (ornithine decarboxylase) which confers resistance to the ornithine decarboxylase inhibitor, 2-(difluoromethyl)-DL-ornithine, DFMO (McConlogue, *Curr. Comm. Mol. Biol.* (Cold Spring Harbor Laboratory Press, 1987), also have been described.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be cotransformed with DNA sequences encoding the sorcin proteins of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Gluzman, *Eukaryotic Viral Vectors* (Cold Spring Harbor Laboratory Press, 1982)).

Sorcin is an EF-hand protein that confers the property of caffeine-activated intracellular $Ca^{2+}$ release in non-muscle cells by interacting with the RyR2. To determine if sorcin could improve the contractile function of the heart, viral vectors (adenoviral or adeno associated virus) containing the transgene sorcin were administered to the heart. In such an administration, the viral vector infects the cardiac myocyte and expresses the transgene sorcin. Sorcin then associates with proteins involved in cardiac myocyte handling. Under the influence of the increased sorcin expression, the calcium release during systole is increased, but also the calcium reuptake into the sarcoplasmic reticulum during dia'stole is improved. This leads to an overall increase in cardiac pump function by improving the calcium handling in the failing heart.

To determine if increasing sorcin levels resulted in altered contractile function, expression of this protein was increased by an in vivo adenoviral-vector mediated gene transfer approach and analyzed cardiac contractility in the isolated perfused heart after 5 days of Adv-sorcin administration. FIG. 1 shows LV pressure, maximum speed of contraction (+dP/dt) and maximum speed of relaxation (−dP/dt) of isolated perfused hearts obtained from normal mice that received either Adv-sorcin or Adv-control). Overexpression of sorcin in the heart resulted in a 40% increase in LV developed pressure (FIG. 1A), 54% in max dP/dt (FIG. 1B) and 72% in min dP/dt (FIG. 1C) compared with the control group (158.3±18.2 vs. 113.3±9.1, 8099±1428 vs. 5250±763, 5231±891 vs. 3034±464, respectively). These data demonstrate that increased expression of cardiac sorcin via gene therapy techniques leads to increased contractility.

Figure 2:
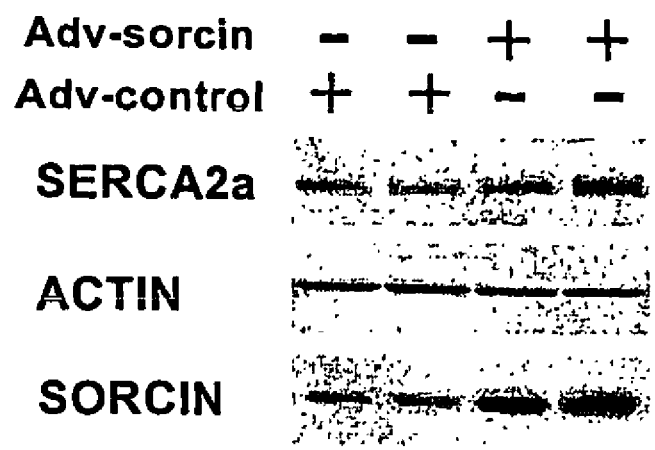
FIG. 2 illustrates sorcin overexpression in the heart after 5 days of adenovirus based sorcin transgene expression. Western blot showing SERCA2a and sorcin proteins detected in heart tissue from Adv-control or Adv-sorcin injected mice. Alpha-actin was used as a control for protein load.

To verify increased expression of sorcin protein after intramyocardial injection in the Adv-Sorcin group, Western blot analysis was performed in cardiac homogenates. FIG. 2 shows an increase of sorcin in ventricular tissue taken from hearts that received Adv-sorcin compared with those that received Adv-control. An increase of 274% in sorcin protein expression was observed in hearts that received Adv-sorcin (3,493±227 vs. 13,058±1974 arbitrary units for control and sorcin respectively, p<0.001, n=10).

Figure 3:
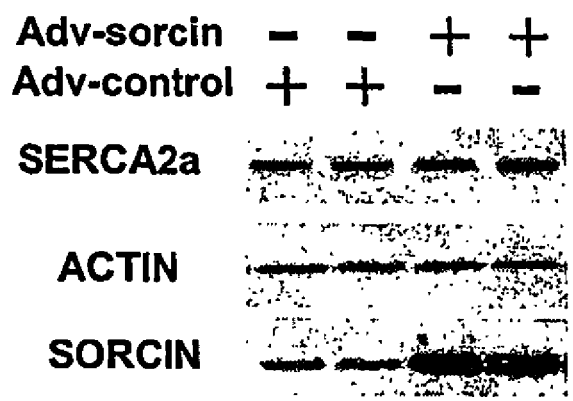
FIG. 3 illustrates sorcin overexpression in adult rat cardiac myocytes infected with Adv-sorcin. Western blots of SERCA2a and sorcin proteins detected in adult rat cardiomyocytes are shown. Alpha-actin was used as a control for protein load. Sorcin levels are markedly increased but SERCA2a and Actin levels are unchanged.
Figure 4:
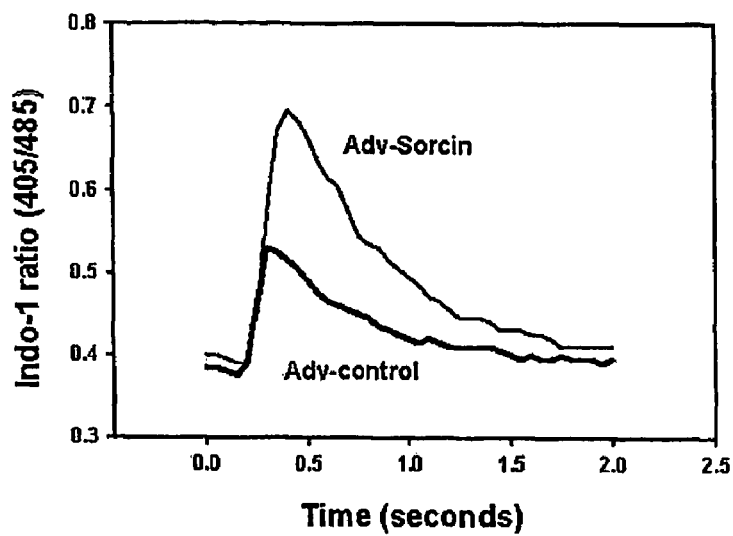
FIG. 4 illustrates the effects of sorcin overexpression on calcium transient. Superimposed original tracings of cytosolic $Ca^{2+}$ transients in a representative sorcin-overexpressing (Adv-sorcin) and control transefected (Adv-control) cardiomyocytes. Myocytes were infected with Adv-control or Adv-sorcin and electrically paced at 0.3 Hz.

It has been demonstrated that sorcin interacts with proteins involved in $Ca^{2+}$ handling for example the ryanodine receptor of the sarcoplasmic reticulum (RyR2) (9) and L-type calcium channels (14). Such interactions could conceivably be affecting $Ca^{2+}$ handling in sorcin-infected cardiomyocytes and be responsible for the increase in contractility. Therefore, it was tested whether sorcin overexpression could alter calcium handling. Infection of adult rat myocytes with Adv-sorcin increased expression of sorcin compared to myocytes infected with control Adv as detected by Western blot (FIG. 3). Analysis of intracellular $Ca^{2+}$ cycling in adult cardiac myocyte 2 days after Adv-sorcin infection revealed significant increases in both diastolic and maximal systolic indo-1 fluorescence ratios (FIG. 4 and Table 1). In addition, the half time of $[Ca^{2+}]$ decline ($t_{1/2}$) in sorcin treated cell was reduced when compared to control cells (0.375±0.018 and 0.320±0.016 respectively, Table 1). In contrast, the time to reach peak systolic $Ca^{2+}$ ($T_{max}$) was found to be increased by approximately 14% in sorcin infected cardiac myocytes (Table 1).

TABLE 1

Effects of Sorcin overexpression on $[Ca^{2+}]_i$ of adult rat ventricular cardiomyocytes.

| CONDITION | $R_{dia}$ | $R_{sys}$ | $T_{max}$ (seconds) | $t_{1/2}$ (seconds) |
|---|---|---|---|---|
| Control (20) | 0.380 ± 0.004 | 0.515 ± 0.016 | 0.172 ± 0.007 | 0.375 ± 0.018 |
| Sorcin (20) | 0.399 ± 0.007* | 0.640 ± 0.031* | 0.194 ± 0.004** | 0.320 ± 0.016* |

Figure 5:
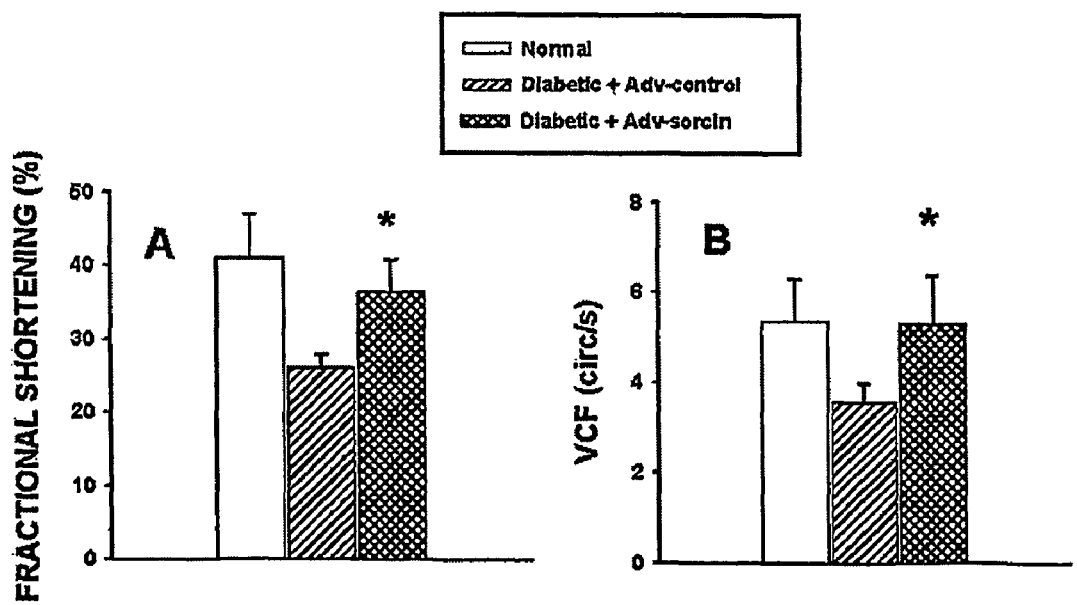
FIG. 5 illustrates the effects of increased sorcin expression on cardiac performance of diabetic mouse hearts in vivo. Echocardiographic measurements of: a) the percent fractional shortening (% FS), and b) velocity of circumferential fiber shortening (Vcf) in mice were performed five days after adenoviral injection of either Adv-sorcin or Adv-control as a control group. Measurements were also performed in a group of normal mice that received Adv-control. Both % FS and Vcf were significant improved in diabetic hearts by increased sorcin expression (*$p<0.005$, n=5 for each group).

$R_{dia}$ and $R_{sys}$ represent the diastolic and maximal systolic indo-1 ratios for electrically paced (0.3 Hz) myocytes infected with Adv-SR- (control) or Adv-sorcin (sorcin).
$T_{max}$ represents the time to reach peak systolic $Ca^{2+}$ ($R_{sys}$).
$t_{1/2}$ represents half life for intracellular $Ca^{2+}$ decline.
Data are mean ±SE for the number of cells indicated in parenthesis.
*P < 0.05 vs. control
**P < 0.001 vs. control Since sorcin overexpression improved cardiac performance in normal mice, probably by enhancing cytosolic calcium transient in the myocyte, it was investigated whether overexpression of sorcin via in vivo-cardiac adenoviral gene delivery may improve the diminished cardiac contractile function observed in the diabetic mice. Transthoracic echocardiography was used for in vivo evaluation of cardiac function. Mice were studied five days after adenoviral infection. Heart failure in the diabetic mice is characterized by a marked decrease in both, percent fractional shortening (% FS) of the left ventricle (LV) and velocity of circumferential fiber shortening (Vcf) (FIG. 5). Adv-sorcin gene therapy rescued cardiac function by returning these parameters to the normal range as shown in FIG. 5 panel A. Especially the left ventricular fractional shortening (% FS) and the velocity of circumferential fiber shortening were significant higher (FIG. 5 panel B). These data demonstrate that sorcin overexpression can counteract the pathological effects of diabetes on cardiac function by augmenting contractility.

Therefore, as determined by the examples below and the results set forth above, the effects of in vivo cardiac adenoviral gene transfer of sorcin on the contractile properties of the mouse heart under both physiological and pathological conditions were determined, and the influence of overexpression of sorcin on calcium transients of adult cardiac myocytes using adenoviral vector based expression of sorcin was determined. The results demonstrate that sorcin enhances cardiac contractile performance in the normal mouse heart. In addition, sorcin can also improve the decreased contractile function of the diabetic heart by enhancing the $Ca^{2+}$ upstroke phase of the calcium transient which is diminished in diabetic cardiac myocytes.

The findings show that increased expression of sorcin results in an enhanced peak of the systolic or upstroke phase of the calcium transient. Commensurate with these changes, an increase in systolic contractile performance occurs as indicated by enhanced fractional shortening, circumferential fiber shortening and dP/dt max. This positive effect of sorcin on contraction may be expected since it has been demonstrated that introduction of sorcin into nonmuscle cells augments caffeine-activated intracellular $Ca^{2+}$ release, suggesting a role for sorcin in modulating RyR2 function (13). In agreement with these findings, an increase in systolic calcium of adult rat cardiomyocytes after sorcin gene transfer (FIG. 4) was observed. Since sorcin inhibits ryanodine binding to cardiac RyR2 and substantially decreases the open probability of the $Ca^{2+}$ release channels reconstituted in lipid bilayers (9) one may expect a decrease in the magnitude of the systolic calcium transient, however, the opposite effect was observed.

While not wanting to be bound by a particular theory, it is believed that an explanation for the effect of sorcin could be that the decrease in calcium release due to the decrease of the open probability of the RyR2 were quickly compensated by an increase in SR $Ca^{2+}$ content which in turn, would lead to an increase in the systolic calcium transient. A delay in $T_{max}$ was found, consistent with delays in RyR2 opening but an increase in diastolic and systolic $[Ca2+]_i$. It is possible that long term exposure to sorcin or maneuvers that decrease the open probability of RyR2 may lead to higher $[Ca^{2+}]_i$. It has been reported that overexpression of FK506-binding protein (FKBP12.6), which also decreases the open probability of the RyR2, stabilizing it in the closed conformational state, provokes an increase in amplitude of twitch shortening in single cardiomyocytes associated to a reduced RyR2-mediated $Ca^{2+}$ efflux from SR and a higher SR—$Ca^{2+}$ load (18). Thus, FKBP12.6 has been proposed to diminish the $Ca^{2+}$ leak from the SR (26). Therefore, a putative role for sorcin would be to function as an inhibitor of SR calcium release similar to FKBP12.6 (3, 25). An effect on SERCA2a may be involved since it was found that $t_{1/2}$ was decreased in cardiac myocytes transfected with sorcin (Table). In addition, dP/dt min was also increased in perfused hearts overexpressing sorcin (FIG. 1C). However, no changes in SERCA2a protein levels, as determined by Western blot, were observed after sorcin overexpression (FIG. 2,3).

Diabetic cardiomyopathy is characterized by reduced cardiac contractility due to direct changes in heart muscle function independent of vascular disease (1, 19). An important contributor to contractile dysfunction in the diabetic state is an abnormal $Ca^{2+}$ handling with diminished $Ca^{2+}$ entry into the cytoplasm during systole and delayed lowering of diastolic $Ca^{2+}$ levels. A diminished number of ryanodine receptors, increased phophorylation of RyR2 as well as diminished SERCA2a activity and expression are important contributors of the abnormal calcium handling in diabetes (4,16,22). Since sorcin improved cardiac contraction in the normal mouse heart, by enhancing calcium transients in the cardiomyocytes, it was investigated whether adenoviral based sorcin expression could ameliorate the diabetes-induced contractile failure. Five days after administration of Adv expressing sorcin to diabetic mice, contractile function was markedly improved as determined by echocardiography. In recent studies, it has been demonstrated that overexpression of SERCA2a improves myocardial contractility in diabetic mice (23). Sorcin did not affect SERCA2a expression in the normal adult rat cardiomyocyte. However, dP/dt min and $t_{1/2}$ were improved by sorcin suggesting an increase in SERCA2a activity. Therefore, the recovery of the impaired sarcoplasmic reticulum function and consequently, the improvement of contractile properties of the diabetic mice may be partially due to an effect of sorcin on SERCA2a activity. The diastolic $Ca^{2+}$ leak from SR is believed to occur through RyR2 (2, 3). Under normal conditions the SR $Ca^{2+}$ leak does not constitute a problem for the cell since it is rapidly compensated by calcium reuptake by SERCA2a (3). In situations like heart failure, which is associated with a downregulation of the activity and expression of SERCA2a, the SR $Ca^{2+}$ leak may contribute to the abnormal calcium handling (26). Both, sorcin and FKBP12.6 may function as a break of the RyR2 preventing $Ca^{2+}$ leak from the SR under normal conditions. However in heart failure, including diabetic cardiomypoathy, hyperphosphorylation of RyR2 occurs resulting in the dissociation of FKBP12.6 and the loss of its RyR2 gating function and a significant SR calcium leak. An approach to overcome this problem is increasing the amount of sorcin protein facilitating the interaction with its target. Sorcin adenoviral gene transfer dramatically increased sorcin expression in the mouse hearts (FIG. 2) and improved contractility in the normal and diabetic mouse heart.

In one aspect, the invention provides a screening assay that includes contacting a test agent with the heart or heart tissue or heart cells of a subject and measuring the maximum speed of contraction and the maximum speed of relaxation in the heart. An increase or decrease in maximum speed is indicative of an agent that modulates cardiac contractile function. Further, screening assays of the invention may be used to identify agents that modulate sorcin expression in the heart of a subject, thereby modulating cardiac contractile function. As disclosed herein, a screening assay of the invention can be performed in vitro (e.g., in a cell free system using purified or partially purified components) or in a cell (e.g., in a cell or tissue culture system or whole organ (e.g. heart).

A screening assay of the invention also provides a means to determine an amount of a particular agent useful for effecting a desired change in sorcin expression, thereby modulating cardiac contractile function. Such a method can be performed by contacting a sample with different amounts of the same or different test agents or different amounts of the same or different agents previously identified as modulating sorcin expression in the heart of a subject. As such, the methods of the invention can be used to confirm that an agent suspected of having a particular activity, in fact, has the activity, thus providing a means, for example, to standardize the activity of the agent.

A sample that is examined according to a method of the invention can be any sample that contains, or to which can be added, cardiac cells expressing sorcin. In one aspect, the sample is a biological sample, including, for example, a bodily fluid; an extract from a cell, which can be a crude extract or a fractionated extract; a chromosome, an organelle or a cell membrane; a cell; genomic DNA, RNA, or cDNA, which can be in solution or bound to a solid support; a tissue; or a sample of an organ. A biological sample, for example, from a human subject, can be obtained using well known and routine clinical methods (e.g., a biopsy procedure).

As used herein, the term "test agent" means any compound or agent that is being examined for the ability to modulate sorcin expression. A test agent (and an agent that modulates sorcin expression identified by a method of the invention) can be any type of molecule, including, for example a peptide, a polynucleotide (including antisense or RNAi), an antibody, a glycoprotein, a carbohydrate, a small organic molecule, or a peptidomimetic.

Where a test agent is identified as modulating expression of sorcin, thereby altering cardiac contractile function, a screening assay of the invention can further include a step of determining an amount by which the agent increases or decreases sorcin expression. For example, where an agent is identified that increases sorcin expression in the heart of a subject, a method of the invention can further include determining an amount by which the agent increases sorcin above a basal level in a corresponding normal sample. Such an agent can be identified by measuring the amount of sorcin in a single sample both before adding the test agent and after adding the test agent, or can be identified for example, using two samples, wherein one sample serves as a control (no test agent added) and the other sample includes the test agent. As such, a method of the invention provides a means to obtain agents or panels of agents that variously modulate sorcin expression, thereby altering cardiac contractile function.

As used herein, a "corresponding normal sample" is any sample taken from a subject of similar species that is considered healthy or otherwise not suffering from cardiomyopathy or a related disorder. As such, a normal/standard level of sorcin expression denotes the level of sorcin present in a sample from the normal sample. A normal level of sorcin can be established by combining body fluids or cell extracts taken from normal healthy subjects, preferably human, with antibody to sorcin under conditions suitable for sorcin expression. Levels of sorcin in subject, control, and disease samples from biopsied tissues can be compared with the standard values. Deviation between standard and subject values establishes the parameters for diagnosing disease. A normal level of sorcin also can be determined as an average value taken from a population of subjects that is considered to be healthy, or is at least free of a cardiac contractile function associated disorder. A variety of protocols including ELISA, RIA, and FACS are useful for measuring levels of sorcin, and provide a basis for diagnosing altered or abnormal levels of sorcin.

As disclosed herein, the screening methods of the invention provide the advantage that they can be adapted to high throughput analysis and, therefore, can be used to screen combinatorial libraries of test agents in order to identify those agents that can modulate sorcin expression. Methods for preparing a combinatorial library of molecules that can be tested for a desired activity are well known in the art and include, for example, methods of making a phage display library of peptides, which can be constrained peptides (see, for example, U.S. Pat. Nos. 5,622,699; 5,206,347; Scott and Smith, *Science* 249:386-390, 1992; Markland et al., *Gene* 109:13 19, 1991; each of which is incorporated herein by reference); a peptide library (U.S. Pat. No. 5,264,563, which is incorporated herein by reference); a peptidomimetic library (Blondelle et al., *Trends Anal. Chem.* 14:83 92, 1995; a nucleic acid library (O'Connell et al., *Proc. Natl. Acad. Sci., USA* 93:5883-5887, 1996; Tuerk and Gold, *Science* 249:505-510, 1990; Gold et al., *Ann. Rev. Biochem.* 64:763-797, 1995; each of which is incorporated herein by reference); an oligosaccharide library (York et al., *Carb. Res.*, 285:99 128, 1996; Liang et al., *Science,* 274:1520 1522, 1996; Ding et al., *Adv. Expt. Med. Biol.* 376:261 269, 1995; each of which is incorporated herein by reference); a lipoprotein library (de Kruif et al, *FEBS Lett.* 399:232 236, 1996, which is incorporated herein by reference); a glycoprotein or glycolipid library (Karaoglu et al., *J. Cell Biol.* 130:567 577, 1995, which is incorporated herein by reference); or a chemical library containing, for example, drugs or other pharmaceutical agents (Gordon et al., *J. Med. Chem.* 37:1385-1401, 1994; Ecker and Crooke, *BioTechnology* 13:351-360, 1995; each of which is incorporated herein by reference). Polynucleotides can be particularly useful as agents that can modulate a specific interaction of molecules because nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference).

In performing a screening assay of the invention in a high throughput (or ultra-high throughput) format, isolated cell membranes or intact cells can be used. An advantage of using intact cells is that the method can be used, for example, to identify an agent useful for modulating sorcin expression within the cell. Any number of samples (e.g., 96, 1024, 10,000, 100,000, or more) can be examined in parallel using such a method, depending on the particular support used.

A particular advantage to high throughput screening finds application to the design of personalized medicine. For example, a plurality of test agents can be arranged in an array, which can be an addressable array, on a solid support such as a microchip, on a glass slide, on a bead, or in a well, and the cells of a subject (e.g., a biopsy sample) can be contacted with the different test agents to identify one or more agents having desirable characteristics, including, for example, in addition to the ability to modulate sorcin expression, minimal or no toxicity to the cell, desirable solubility characteristics, and the like. Consequently, a treatment regimen may be tailored specifically to the individual based upon the subject's levels of sorcin expression.

An additional advantage of arranging the samples in an array, particularly an addressable array, is that an automated system can be used for adding or removing reagents from one or more of the samples at various times, or for adding different reagents to particular samples. In addition to the convenience of examining multiple test agents and/or samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays.

Various protocols may be employed for screening a library of chemical compounds. To some degree, the selection of the appropriate protocol will depend upon the nature of the preparation of the compounds. For example, the compounds may be bound to individual particles, pins, membranes, or the like, where each of the compounds is segregatable. In addition, the amount of compound available will vary, depending upon the method employed for creating the library. Furthermore, depending upon the nature of the attachment of the compound to the support, one may be able to release aliquots of a compound, so as to carry out a series of assays. In addition, the manner in which the compounds are assayed will be affected by the ability to identify the compound which is shown to have activity.

Where the agents are individually located on a surface in a grid, so that at each site of the grid one knows the identification of each agent, one can provide a cellular lawn which is similarly organized as a grid and may be placed in registry with the agents bound to the solid surface. Once the lawn and solid substrate are in registry, one may release the agents from the surface in accordance with the manner in which the agents are attached. After sufficient time for the agents to bind to the proteins on the cellular surface, one may wash the cellular lawn to remove non-specifically bound agents. One or more washings may be involved, where the washings may provide for varying degrees of stringency, depending upon the desired degree of affinity. Since the preparative process can be repeated, a plurality of solid substrates can be prepared, where the same compounds are prepared at the comparable sites, so that the screening could be repeated with the same or different cells to determine the activity of the individual compounds.

In some instances, the identity of the agent can be determined by a nucleic acid tag, using the polymerase chain reaction for amplification of the tag. See, for example, WO93/20242. In this instance, the agents which are active may be determined by taking the lysate and introducing the lysate into a polymerase chain reaction medium comprising primers specific for the nucleic acid tag. Upon expansion, one can sequence the nucleic acid tag or determine its sequence by other means, which will indicate the synthetic procedure used to prepare the agent.

Alternatively, one may have tagged particles where the tags are releasable from the particle and provide a binary code which describes the synthetic procedure for the compounds bound to the particle. See, for example, Ohlmeyer, et al., PNAS USA (1993) 90:10922. These tags can conveniently be a homologous series of alkylene compounds, which can be detected by gas chromatography-electron capture. Depending upon the nature of the linking group, one may provide for partial release from the particles, so that the particles may be used 2 or 3 times before identifying the particular compound.

While for the most part libraries have been discussed, any large group of compounds can be screened analogously, so long as the sorcin molecule can be joined to each of the compounds. Thus, compounds from different sources, both natural and synthetic, including macrolides, oligopeptides, ribonucleic acids, dendrimers, etc., may also be screened in an analogous manner.

Sorcin expression represents a specific target for the development of anti-cardiomyopathy therapeutics. Accordingly, the invention provides methods of using of an agent that can modulate sorcin expression to treat a cardiac contractile function associated disorder. As such, the methods provide for the administration of a therapeutically effective amount of an agent that modulates sorcin expression.

For administration to a subject, an agent that modulates sorcin expression is administered by a route and under conditions that facilitate contact of the agent with the target cell and, if appropriate, entry into the cell. Thus, the agent can be administered to the site of the cells to be treated, or can be administered by any method that provides the target cells with the agent. Furthermore, the agent generally is formulated in a composition (e.g., a pharmaceutical composition) suitable for administration to the subject. As such, the invention provides pharmaceutical compositions containing an agent that modulates sorcin expression in a pharmaceutically acceptable carrier. As such, the agents are useful as medicaments for treating a subject suffering from heart failure resulting from a cardiac contractile function associated disorder. Further, such a composition -pan include one or more other compounds that, alone or in combination with the agent that modulates sorcin expression, provides a therapeutic advantage to the subject, for example, an antibiotic if the subject is susceptible to a bacterial infection, one or more additional antiviral agents known to be useful for treating the particular disease or disorder, a nutrient or vitamin or the like, a diagnostic reagent, toxin, a therapeutic agent such as a cancer chemotherapeutic agent, or any other compound as desired, provided the additional compound(s) does not adversely affect the activity of the agent that modulates sorcin expression or, if the compound does affect the activity of the agent, does so in a manner that is predictable and can be accounted for in formulating the agent.

Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the agent that alters protein-protein interactions that affect hearing and on the route of administration of the composition, which can be, for example, orally or parenterally such as intravenously, and by injection, intubation, or other such method known in the art.

An agent that modulates sorcin expression can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley et al., *Trends Biochem. Sci.* 6:77, 1981, each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a composition useful for practicing a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.* 91:2580-2585, 1993, which is incorporated herein by reference). In addition, a polynucleotide agent can be introduced into a cell using, for example, adenovirus-polylysine DNA complexes (see, for example, Michael et al., *J. Biol. Chem.* 268:6866-6869, 1993, which is incorporated herein by reference).

The route of administration of a pharmaceutical composition containing an agent that modulates sorcin expression as discussed herein will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are well known (see, for example, Blondelle et al., supra, 1995; Ecker and Crook, supra, 1995). In addition, a peptide agent can be prepared using D-amino acids, or can contain one or more domains based on peptidomimetics, which are organic molecules that mimic the structure of peptide domain; or based on a peptoid such as a vinylogous peptoid.

A pharmaceutical composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the pharmaceutical composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tissue or organ comprising retrovirus infected cells.

The pharmaceutical composition also can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The present invention also provides methods for diagnosing cardiac contractile function associated disorders in a subject. In one embodiment, agents identified as modulating sorcin expression may be used for the diagnosis of conditions or diseases characterized by cardiac contractile function associated disorders, or in assays to monitor patients being treated for heart failure. The agents useful for diagnostic purposes may be prepared in the same manner as those described above for therapeutics. Diagnostic assays for cardiac contractile function associated disorders include methods which utilize the identified agents and a label to detect sorcin expression m samples such as human body fluids or extracts of cells or tissues. The agents may be used with or without modification, and may be labeled by joining them, either covalently or non-covalently, with a reporter molecule. A wide variety of reporter molecules which are known in the art may be used.

The total amount of an agent that modulates sorcin expression to be administered in practicing a method of the invention can be administered to a subject as a single dose, either as a bolus or by infusion over a relatively short period of time, or can be administered using a fractionated treatment protocol, in which multiple doses are administered over a prolonged period of time. An advantage of using a fractionated method is that, upon normal division of a retrovirus infected cell, replication of the retrovirus can be reduced or inhibited due to the presence of the agent. One skilled in the art would know that the amount of the composition to treat a retrovirus infection in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration for treatment of human subjects are determined, initially, using Phase I and Phase II clinical trials.

Once disease is established and a treatment protocol is initiated, screening assays of the invention may be repeated on a regular basis to evaluate whether the level of sorcin expression and/or cardiac contractile function in the patient begins to approximate that which is observed in the normal patient. The results obtained from successive assays may be used to show the efficacy of treatment over a period ranging from several days to months. Accordingly, the invention is also directed to methods for monitoring a therapeutic regimen for treating a subject having heart failure. A comparison of the cardiac contractile function prior to and during therapy indicates the efficacy of the therapy. Therefore, one skilled in the art will be able to recognize and adjust the therapeutic approach as needed The present invention establishes that sorcin overexpression enhances cardiac contractile performance and establishes the concept of sorcin as a regulator of myocardial contractility. The mechanism of action of sorcin involves regulation of cytosolic calcium fluxes. Viral vector based delivery of specific proteins improving $Ca^{2+}$ flux, such as sorcin, provide a novel approach to improve contractile function in different pathophysiological conditions including diabetic cardiomyopathy.

The following examples are intended to illustrate but not limit the invention.

EXAMPLE 1

Preparation of Mice

Three categories of mice were prepared and utilized: Normal mice receiving the empty construct adenovirus control, diabetic mice receiving the empty construct adenovirus control and diabetic mice receiving adenovirus sorcin. The mice were prepared as follows.

Adenovirus mice were prepared by anesthetizing normal mice with a ketamine (100 mg/kg), xylazine (8 mg/kg) mixture, intubating and ventilating with room air. The heart was exposed by a lateral sternotomy at the level of the second intercostal space. Adenovirus (Adv) was administered by direct injection into the left ventricular free wall of mice heart at 5 sites with 10 µl of $10^{11}$ pfu/ml per site using an insulin syringe with a 29 gauge needle. This method allowed the infection of approximately 50% of the myocytes in the left ventricle. After closing the thoracic cavity, the mice were extubated and allowed to recover for 5 days.

Mice were made diabetic by the injection (i.p.) of 200 mg/kg streptozotocin 3 weeks prior to surgery as described previously (23). Diabetic mice had blood glucose levels in excess of 600 mg/dl while non-diabetic mice had levels of 216 mg/dl. Adenovirus administration was performed as described for normal mice.

In order to study the effects of sorcin expression in vivo, the gene coding for sorcin was cloned into a replication deficient adenoviral vector under control of the promoter-enhancer region of the human cytomegalovirus (Adv-sorcin). The general procedure has been previously described (7). An empty adenovirus without transgene (Adv-control) was injected in the control group.

Five days after viral vector injection, hearts were isolated and transferred to a miniaturized Langendorff set-up for contractile studies in isolated mouse hearts as previously described (24). In brief, hearts were removed from anesthetized mice and immersed in cold Krebs Henseleit buffer solution. The aorta was cannulated and Langendorff perfusion was initiated with Krebs Henseleit buffer at a perfusion pressure of 55 mmHg. A small fluid filled balloon was inserted into the left ventricle (LV) and inflated to an end diastolic pressure of 10 mmHg. Pressure development was recorded digitally by connecting the intraventricular balloon to a 2 French Millar catheter. The hearts were paced at 400 bpm and the resulting pressure waves were analyzed for pressure derivatives (+dP/dt, −dP/dt) and peak systolic pressure. At the end of the experiment, hearts were frozen in liquid $N_2$ for Western analysis of protein expression.

In vivo cardiac performance was determined by echocardiography in the three groups: 1) diabetic mice receiving Adv-sorcin, 2) diabetic mice receiving the empty construct Adv-control, and 3) normal mice receiving the empty construct Adv-control. Transthoracic echocardiography was performed as previously described (21). For acquisition of in vivo cardiac functional data an Apogee CX (ATL Interspec) echocardiography system was used. For image acquisition, mice were anesthetized with Avertin 2.5% (10 μl/g body weight). The mice were placed in the left lateral decubitus position and the transducer placed on the left hemithorax. Care was taken not to apply excessive pressure on the chest to avoid bradycardia. The 2D parasternal short-axis view was used as a guide and a LV M-mode tracing was obtained close to the papillary muscle level with a sweep speed of 100 mm/s. Pulsed Doppler tracings of the estimated LV outflow tract velocity were obtained in a modified parasternal long-axis view at a sweep speed of 100 mm/s. M-mode and Doppler tracings were recorded on a video tape for off-line analysis on an Agilent Sonos 5500 system. After calibration of this system, left ventricular end-diastolic and end-systolic internal diameter (LVEDD and LVESD respectively) were measured in three consecutive heart cycles using the American Society of Echocardiography leading-edge method (20). LV fractional shortening was calculated as FS (%)=(LVEDD−LVESD)/LVEDD×100. Using the mean aortic ejection time (ET) from three consecutive heart cycles obtained from the Doppler tracings of the LV outflow tract, the velocity of circumferential fiber shortening (Vcf) as Vcf (circ/s)= (πLVEDD−πLVESD)/(ET×πLVEDD) was calculated. Being sensitive to acute changes in loading conditions, mean Vcf provides an approach for in vivo assessing myocardial contractility under basal conditions without acute changes in arterial pressure (10).

Following SDS-PAGE and transfer to nitrocellulose, membranes were incubated with the appropriate antibodies. The primary antibody was a rabbit anti-sorcin polyclonal antibody provided as a kind gift by Dr. Hector Valdivia. The secondary antibody was a horseradish peroxidase conjugated anti-rabbit.

EXAMPLE 2

Isolation and Adenoviral Infection of Adult Ventricular Rat Cardiomyocytes $Ca^{2+}$ tolerant adult cardiomyocytes were isolated from ventricular tissue of rats by standard enzymatic digestion procedure (8) and cultured on 4 well Lab-Tek chambered coverglass system treated with laminin (Nalge Nunc Inc., IL, USA). Cells were infected with either Adv-sorcin or Adv-control 2h after isolation with a multiplicity of infection of 20 pfu/cell. Calcium-transients were-determined 48 hr after infection.

The indo 1-facilitated $Ca^{2+}$ transient measurement after adenoviral infection was performed as described previously (5). In brief, cells cultured on chambered coverglass were loaded with indo-1 (3 micromolar indo-1/AM) via 20-min incubations at room temperature in an atmosphere of 5% $CO_2$/95% air. The dispersing agent, Pluronic F-127 (BASF Wyandotte, Wy-andotte, MI, USA), was also present during indo-1 loading at a final concentration of 0.02 mg/ml. Chambers were rinsed to remove excess indo-1/AM and mounted in a Nikon Diaphot epi-fluorescence microscope equipped with a 100× fluor objective (oil immersion) interfaced to a Solamere Technologies, Inc. (Salt Lake City, Utah, USA) dual emission lamp, with the excitation wavelength set to 365 nm via a filter. Fluorescence emission was split and directed to two photomultiplier tubes with 20-nm band-pass filters centered at 405 and 485 nm, respectively. Additionally, an aperture mechanism allowed fluorescence to be collected from a selected portion of the field, which was always positioned over the cytoplasmic region of individual cells. Data were simultaneously collected from each emission channel at a rate of 20 Hz. Fluorescence measurements were performed in Tyrode's buffer with 2 mM $CaCl_2$ containing 25 mM HEPES at room temperature beginning 15-20 min after loading with indo-1. For each well, measurements were typically carried out for 10-20 s on an individual cell, a time period during which there was minimal photobleaching of indo-1. This was repeated with additional cells in other fields so that a total of up to 20 cells after infection with Adv expressing sorcin or empty Adv were surveyed. Indo-1 fluorescence data are reported here as ratios of fluorescence simultaneously obtained from the 405 and 485 nm channels, providing for relative comparisons of the cytoplasmic calcium concentration between experimental treatments.

REFERENCES

1. Ahmed S S, Jaferi G A, Narang R M, and Regan T J. Preclinical abnormality of left ventricular function in diabetes mellitus. *Am Heart J* 89: 153-158, 1975.
2. Bassani R A and Bers D M. Rate of diastolic Ca release from the sarcoplasmic reticulum of intact rabbit and rat ventricular myocytes. *Biophys J* 68: 2015-2022, 1995.
3. Bers D M. *Excitation-contraction coupling and cardiac contractile force*. Dordrecht; Boston: Kluwer Academic Publishers, 2001.
4. Ganguly P K, Pierce G N, Dhalla K S, and Dhalla N S. Defective sarcoplasmic reticular calcium transport in diabetic cardiomyopathy. *Am J Physiol* 244: E528-535, 1983.
5. Giordano F J, He. H, McDonough P, Meyer M, Sayen M R, and Dillmann W H. Adenovirus-mediated gene transfer reconstitutes depressed sarcoplasmic reticulumCa2+-ATPase levels and shortens prolonged cardiac myocyte Ca2+ transients. *Circulation* 96: 400-403, 1997.

6. Gracy K N, Clarke C L, Meyers M B, and Pickel V M. N-methyl-D-aspartate receptor 1 in the caudate-putamen nucleus: ultrastructural localization and co-expression with sorcin, a 22,000 mol. wt calcium binding protein. *Neuroscience* 90: 107-117, 1999.
7. He H, Meyer M, Martin J L, McDonough P M, Ho P, Lou X, Lew W Y, Hilal-Dandan R, and Dillmann W H. Effects of mutant and antisense RNA of phospholamban on SR Ca(2+)-ATPase activity and cardiac myocyte contractility. *Circulation* 100: 974-980, 1999.
8. Lew W Y, Lee M, Yasuda S, and Bayna E. Depyrogenation of digestive enzymes reduces lipopolysaccharide tolerance in isolated cardiac myocytes. *J Mol Cell Cardiol* 29: 1985-1990, 1997.
9. Lokuta A J, Meyers M B, Sander P R, Fishman G I, and Valdivia H H. Modulation of cardiac ryanodine receptors by sorcin. *J Biol Chem* 272: 25333-25338, 1997.
10. Mahler F, Ross J, Jr., O'Rourke R A, and Covell J W. Effects of changes in preload, afterload and inotropic state on ejection and isovolumic phase measures of contractility in the conscious dog. *Am J Cardiol* 35: 626-634, 1975.
11. Maki M, Narayana S V, and Hitomi K. A growing family of the Ca2+-binding proteins with five EF-hand motifs. *Biochem J* 328 (Pt 2): 718-720, 1997.
12. Meyers M B. *Novel Calcium-binding proteins: Fundamentals and clinical implications.* Springer-Verlag, 1991.
13. Meyers M B, Pickel V M, Sheu S S, Sharma V K, Scotto K W, and Fishman G I. Association of sorcin with the cardiac ryanodine receptor. *J Biol Chem* 270: 26411-26418, 1995.
14. Meyers M B, Puri T S, Chien A J, Gao T, Hsu P H, Hosey M M, and Fishman G I. Sorcin associates with the pore-forming subunit of voltage-dependent L-type Ca2+channels. *J Biol Chem* 273: 18930-18935, 1998.
15. Meyers M B, Zamparelli C, Verzili D, Dicker A P, Blanck T J, and Chiancone E. Calcium-dependent translocation of sorcin to membranes: functional relevance in contractile tissue. *FEBS Lett* 357: 230-234, 1995.
16. Netticadan T, Temsah R M, Kent A, Elimban V, and Dhalla N S. Depressed levels of Ca2+-cycling proteins may underlie sarcoplasmic reticulum dysfunction in the diabetic heart. *Diabetes* 50: 2133-2138, 2001.
17. Okamoto Y, Chaves A, Chen J, Kelley R, Jones K, Weed H G, Gardner K L, Gangi L, Yamaguchi M, Klomkleaw W, Nakayama T, Hamlin R L, Cames C, Altschuld R, Bauer J, and Hai T. Transgenic mice with cardiac-specific expression of activating transcription factor 3, a stress-inducible gene, have conduction abnormalities and contractile dysfunction. *Am J Pathol* 159: 639-650, 2001.
18. Prestle J, Janssen P M L, Janssen A P, Zeitz O, Lehnart S E, Bruce L, Smith G L, and Hasenfuss G. Overexpression of FK506-Binding Protein FKBP12.6 in Cardiomyocytes Reduces Ryanodine Receptor-Mediated Ca2+ Leak From the Sarcoplasmic Reticulum and Increases Contractility. *Circ Res* 88: 188-194, 2001.
19. Rubler S, Sajadi R M, Araoye M A, and Holford F D. Noninvasive estimation of myocardial performance in patients with diabetes. Effect of alcohol administration. *Diabetes* 27: 127-134, 1978.
20. Sahn D J, DeMaria A, Kisslo J, and Weyman A. Recommendations regarding quantitation in M-mode echocardiography: results of a survey of echocardiographic measurements. *Circulation* 58: 1072-1083, 1978.
21. Tanaka N, Dalton N, Mao L, Rockman H A, Peterson K L, Gottshall K R, Hunter J J, Chien K R, and Ross J, Jr. Transthoracic echocardiography in models of cardiac disease in the mouse. *Circulation* 94: 1109-1117, 1996.
22. Teshima Y, Takahashi N, Saikawa T, Hara M, Yasunaga S, Hidaka S, and Sakata T. Diminished expression of sarcoplasmic reticulum Ca(2+)-ATPase and ryanodine sensitive Ca(2+)Channel mRNA in streptozotocin-induced diabetic rat heart. *J Mol Cell Cardiol* 32: 655-664, 2000.
23. Trost S U, Belke D D, Bluhm W F, Meyer M, Swanson E, and Dillmann W H. Overexpression of the sarcoplasmic reticulum Ca(2+)-ATPase improves myocardial contractility in diabetic cardiomyopathy. *Diabetes* 51: 1166-1171, 2002.
24. Trost S U, Omens J H, Karlon W J, Meyer M, Mestril R, Covell J W, and Dillmann W H. Protection against myocardial dysfunction after a brief ischemic period in transgenic mice expressing inducible heat shock protein 70. *J Clin Invest* 101: 855-862, 1998.
25. Valdivia H H. Modulation of intracellular Ca2+ levels in the heart by sorcin and FKBP12, two accessory proteins of ryanodine receptors. *Trends Pharmacol Sci* 19: 479-482, 1998.
26. Yano M, Ono K, Ohkusa T, Suetsugu M, Kohno M, Hisaoka T, Kobayashi S, Hisamatsu Y, Yamamoto T, Kohno M, Noguchi N, Takasawa S, Okamoto H, and Matsuzaki M. Altered Stoichiometry of FKBP12.5 Versus Ryanodine Receptor as a Cause of Abnormal Ca2+ Leak Through Ryanodine Receptor in Heart Failure. *Circulation* 102: 2131-2136, 2000.
27. Zamparelli C, Ilari A, Verzili D, Vecchini P, and Chiancone E. Calcium- and pH-linked oligomerization of sorcin causing translocation from cytosol to membranes. *FEBS Lett* 409:1-6, 1997.

Although the invention has been described with reference to the above examples, it will be understood that modifications and variations are encompassed within the spirit and scope of the invention. Accordingly, the invention is limited only by the following claims.

What is claimed is:

1. A method of increasing cardiac contractile function in a subject comprising altering the expression of sorcin in the subject's heart by administering a viral vector encoding sorcin to the subject, wherein sorcin expression and contractile function are increased as compared to sorcin expression and contractile function prior to administration.

2. The method of claim 1, wherein the vector is an adenoviral or adeno-associated virus vector.

3. The method of claim 1, wherein the vector is administered directly into the heart.

4. The method of claim 1, wherein the heart is in a normal subject without heart disease.

5. The method of claim 1, wherein the heart has decreased contractile function prior to administration of the viral vector.

6. The method of claim 4, wherein the subject has diabetes mellitus.

7. A method of treating heart failure, comprising administering an adenoviral or adeno-associated virus vector encoding sorcin to a subject, wherein sorcin expression and contractile function are increased as compared to sorcin expression and contractile function prior to administration.

8. The method of claim 7, wherein the vector is administered directly into the heart of the subject.

9. A method for monitoring a therapeutic regimen for treating a subject having heart failure, comprising determining a change in sorcin expression during therapy.

10. The method of claim 9, wherein the therapy comprises the treatment of claim 7.

* * * * *